United States Patent [19]

Maeda et al.

[11] Patent Number: 5,084,275

[45] Date of Patent: Jan. 28, 1992

[54] PROCESSES OF PREPARING α-AMYLASE INHIBITING SUBTANCES FROM WHEAT

[75] Inventors: Koji Maeda, Heidelberg, Australia; Yoshitaka Satoh, Tokorozawa, Japan

[73] Assignee: Nisshin Flour Milling Co., Ltd., Tokyo, Japan

[21] Appl. No.: 447,366

[22] Filed: Dec. 6, 1989

[30] Foreign Application Priority Data

Dec. 9, 1988 [JP] Japan .................. 63-311244

[51] Int. Cl.$^5$ .............................. A61K 35/78
[52] U.S. Cl. ........................ 424/195.1; 530/375
[58] Field of Search .............. 424/195.1; 530/375

[56] References Cited

U.S. PATENT DOCUMENTS

| 4,806,626 | 2/1989 | Maeda et al. | 435/68 |
| 4,859,468 | 8/1989 | Kubo et al. | 424/195.1 |
| 4,931,278 | 6/1990 | Blost et al. | 424/195.1 |

FOREIGN PATENT DOCUMENTS 60-4132A 5/1985 Japan .
63-185995 8/1988 Japan .

OTHER PUBLICATIONS

Biological Abstracts, vol. 77, No. 4, (1984), abstract No. 30591, (Weselake et al.).

Primary Examiner—Jose G. Dees
Assistant Examiner—Vera C. Clarke
Attorney, Agent, or Firm—Michael N. Meller

[57] ABSTRACT

A process of preparing an α-amylase inhibiting substance from wheat is disclosed which comprises heat treating a supernatant fraction of an aqueous extract of wheat or wheat flour to modify unnecessary protein contaminants in the supernatant fraction, removing a modified protein from said fraction, and subjecting a resulting aqueous solution containing an α-amylase inhibiting substance to a concentration treatment using an ultrafiltration membrane. As the ultrafiltration membrane is used the membrane of polyacrylonitrile, polyolefin, polysulfone, polyimide or polypropylene materials, each having a fractionation molecular weight of 5,000, 6,000, 8,000, 10,000, 13,000, 20,000, 30,000, 50,000, 100,000 and 200,000 Dalton cut off.

5 Claims, 1 Drawing Sheet

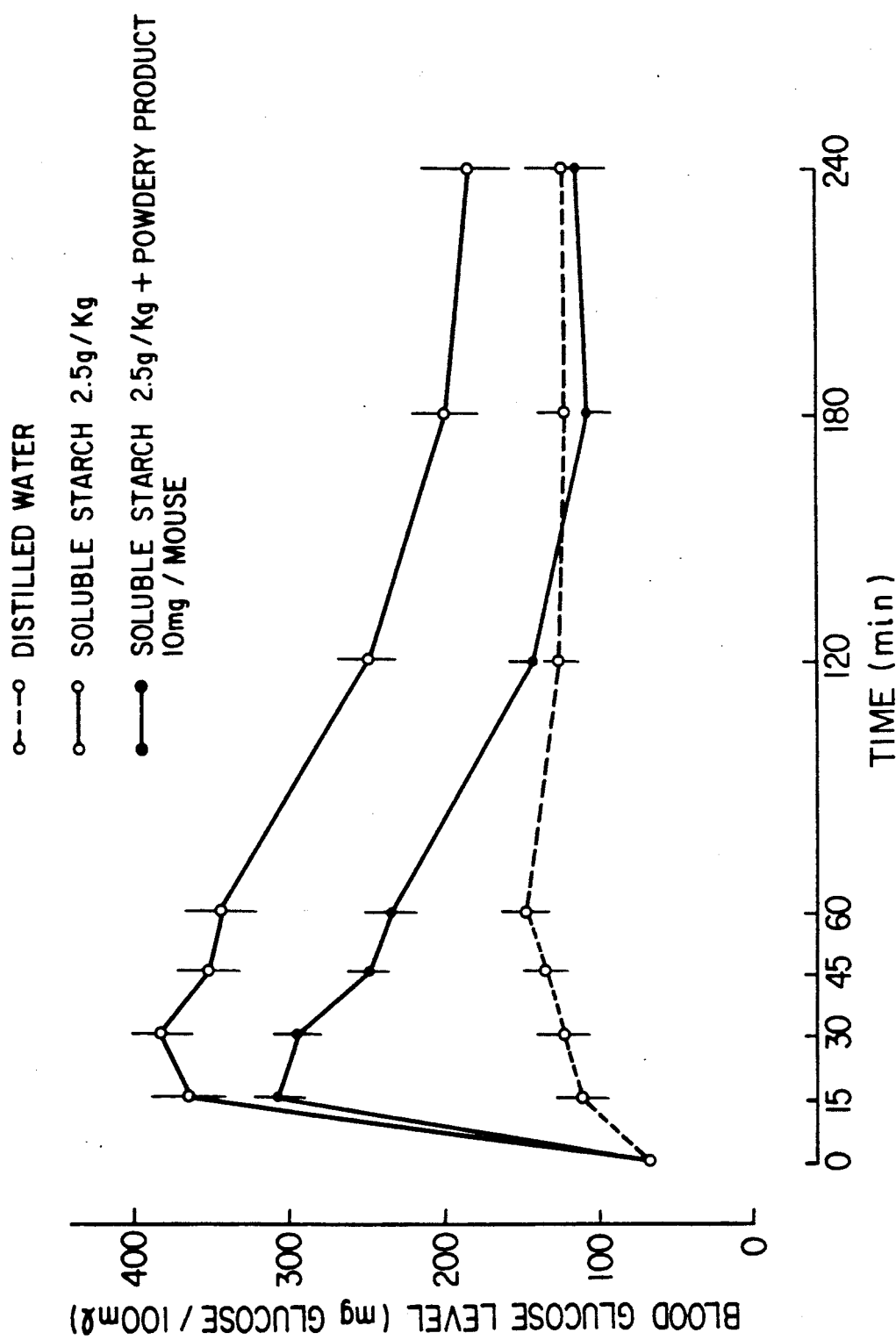

PROCESSES OF PREPARING α-AMYLASE INHIBITING SUBTANCES FROM WHEAT

BACKGROUND OF THE INVENTION

1. Field of the Invention

This invention relates to a process of preparing an α-amylase inhibiting substance from a supernatant of an aqueous extract of wheat or wheat flour.

2. Description of the Prior Art

It is known that wheat or wheat flour contains a large quantity of α-amylase inhibiting substances. Such substances inhibit conversion of starch to saccharides even if sprouting of wheat ears occurs under such weather conditions as much rain in harvest season thereby preventing quality deterioration of the harvested wheat.

On one hand, α-amylase is an enzyme capable of at random hydrolyzing the α-1,4-glycoside bond of starch, glycogen and the like, which is extensively distributed in animals, plants, molds, bacteria, etc. In humans, there are α-amylase of saliva origin and α-amylase of pancreas origin, which play a role in converting starch to saccharides respectively in the mouth and the digestive tracts. Because the α-amylase inhibiting substance inhibits an activity of α-amylase, it is useful as a dieting agent for the prevention of obesity, as therapeutic agents for hyperglycemia and diabetes, as prophylactic agent for dental caries and so on.

In these circumstances, many attempts have been made to produce an α-amylase inhibitor by extraction from various raw materials. There are known a method for the extraction from betel nuts (Japanese Patent LOP Publn. No. 185995/1988) and a method for extracting an α-amylase inhibiting substance contained in wheat (Japanese Patent LOP Publn. No. 140727/1982).

The prior art processes of preparing α-amylase inhibiting substances from wheat or wheat flour include a very complicated operation which comprises a heat treatment of an aqueous extract of wheat or wheat flour, fractional precipitation of the resulting mass with an organic solvent, collecting a precipitated fraction, treating a solution fraction with an adsorbent, eluting an adsorbed substance with a salt solution and fractionating an eluate by chromatography. These processes are not efficient and economical for the production of α-amylase inhibiting substances.

In the manufacture of wheat gluten and wheat starch, a large amount of washing (waste liquid) has been produced from a step of eluting starch from dough or batter formed by kneading flour and water. A treatment of waste liquid needs much labor and cost. This treatment includes a troublesome problem in the industry. Since such waste liquid contains α-amylase inhibiting substances, recovery of the substances from the waste liquid would bring about combined effects of disposing the waste liquid and collecting valuable substances.

SUMMARY OF THE INVENTION

The present invention is directed to a process of preparing an α-amylase inhibiting substance from wheat which comprises heat treating a supernatant fraction of an aqueous extract of wheat or wheat flour to modify unnecessary protein contaminants in the supernatant fraction, removing a modified protein from said fraction, and subjecting a resulting aqueous solution containing an α-amylase inhibiting substance to a concentration treatment using an ultrafiltration membrane.

BRIEF DESCRIPTION OF THE DRAWINGS

FIG. 1 is a graph indicating change of blood glucose level in mice after administration of distilled water, soluble starch and soluble starch plus a powdery product obtained in Example 1, respectively.

DETAILED DESCRIPTION OF THE INVENTION

In the process of the invention, the aqueous solution containing α-amylase inhibiting substances may be subjected to a filtration and sterilization treatment prior to the concentration treatment using an ultrafiltration membrane. Further, the concentrated solution containing α-amylase inhibiting substances may be dried by a conventional method such as spray drying, freeze drying or vacuum drying to form a powdery product.

In a preferred embodiment of the invention, the process comprises the following steps.

(a) Wheat flour and water at a ratio of at least 7:1 are kneaded at a temperature of 0° to 40° C. for a period of 30 min. to 3 hours followed by centrifugation (e.g., 3000 G, 30 min.) or allowing to stand to give a supernatant. The supernatant contains soluble substances such as soluble protein, soluble starch, inorganic salts and coloring matters.

(b) The supernatant is heated at a temperature of 70° to 95° C., preferably 85° to 90° C. to modify unnecessary proteins. The modified proteins are removed by centrifugation (e.g., 3000 G, 30 min.) or allowing to stand.

(c) The resulting supernatant is filtered as it is still hot preferably by filters having a pore size of 3 μm and 1 μm, respectively, to give a clear solution.

(d) Subsequently, the solution is passed through a microfiltration membrane having a pore size of 0.2 μm for sterilization.

(e) The sterilized solution containing α-amylase inhibiting substances is concentrated using an ultrafiltration membrane (preferably, a membrane passing through a fraction having a molecular weight of more than 20,000 to less than 100,000). Inorganic salts and unnecessary low molecular weight substances are removed but α-amylase inhibiting substances do not pass through said membrane. In this step, a volume of the clear solution is concentrated to less than about 1/10 of its original volume.

(f) Optionally, the concentrated solution is dried by a known method such as spray drying, freeze drying or vacuum drying to afford a powdery product.

The supernatant used in the step (a) may be a supernatant separated from a kneaded solution of wheat flour and water for the purpose of recovering α-amylase inhibiting substances or may be a waste liquid after recovery of gluten and starch from wheat.

In the manufacture of gluten and wheat starch, Martin's or Batter's method have been employed. A portion of the water used in such method is carried out of the manufacturing system as moisture to maintain the gluten in its wet state or as moisture contained in the starch cake. The amount of water carried is only slight and the most of water is discharged as a waste liquid. Since such waste liquid contains a large amount of high molecular organic materials such as carbohydrates and proteins in raw form, effective use of them will be advantageous from the standpoint of liquid-waste treatment.

The Martin's and Batter's methods are a method comprising the steps of kneading wheat flour with water to form dough or batter, aging it to thoroughly hydrate gluten, repeatedly washing the dough with added water, separating the gluten and starch milk (gluten wash liquid) and obtaining starch from the starch milk by such means as mechanical separation. In this case, the waste liquid contains the α-amylase inhibiting substance present in wheat flour. Thus such waste liquid can be served as a useful raw material in the process of the invention.

α-Amylase inhibiting substances prepared by the processes of the invention are heat-resistant enzymatic substances and are not denatured when heated. This property is well utilized in the present invention for removal of protein contaminants and other enzymatic substances. When the supernatant in the above step (b) is heated at a temperature of 70° to 95° C., water-soluble proteins and other enzymatic substances undergo heat modification to mostly form muddy precipitates. Such modified proteins can be readily separated by means of standing or centrifugation. In this step, the content of the protein contaminants can be reduced to about $\frac{1}{4}$-1/5 without loss of α-amylase inhibiting substances.

Following step (b), the α-amylase inhibiting substance-containing solution is optionally subjected to the steps (c) and (d) for removing solid contaminants and microbial bodies if present.

One of the characteristic features of the processes according to the invention lies in the subsequent step (e). In this step, ultrafiltration is carried out to remove inorganic salts, saccharides, amino acids and other unnecessary low molecular weight substances while leaving a desired α-amylase inhibiting substances which are concentrated.

The ultrafiltration membranes used in the invention include those of polyacrylonitrile, polyolefin polysulfone, polyimide or polypropylene materials, each having a fractionation molecular weight of 5,000, 6,000, 8,000, 10,000, 13,000, 20,000, 30,000, 50,000, 100,000 and 200,000 Dalton cut off. A polysulfone ultrafiltration membrane having a fractionation molecular weight of 100,000 Dalton cut off (e.g. PM-100 manufactured by Romicon Co., Ltd., NTU 35100 manufactured by Nitto Denko Co., Ltd.) is preferable in view of operativeness and concentration efficiency.

Subsequent to step (e), the concentrated solution is subjected to step (f), if necessary. This step (f) can produce a powdery material which is easily handled and stored.

The α-amylase inhibiting substances have the activities of inhibiting α-amylases contained in saliva and pancreatic juice of animals, which results in decomposition of starch substances contained in food to prevent the digestion and absorption as energy source. Thus, they are effective as a dieting agent, as therapeutic agents for obesity, hyperglycemia and diabetes, as a preventive agent for dental caries and so on.

Representative α-amylase inhibiting substances prepared by the processes of the invention have the following physical properties.

Composition (per 100 g of the powders)
Moisture 2.3 g–3.3 g (Vacuum heating-drying method)
Protein 21.6 g–17.8 g (Kjeldahl's method)
Ash 5.6 g–7.8 g (Direct incineration method)
Sodium 624 mg–139 mg (Atomic absorptiometry)
Potassium 1.41 mg–1.89 mg (Atomic absorptiometry)
Magnesium 356 mg–723 mg (Atomic absorptiometry)
Chlorine 1.43 g–737 mg (Mohr's method)
Total saccharide 57.5 g–56.1 g (Somogyi's method)
Sulfate radical 240 mg–620 mg (Ion chromatography)
α-Amylase Inhibiting Activity (Blue starch method)
Saliva type—5–1 U/mg solid
Pancreatic juice type—3–0.1 U/mg solid The aqueous solution or solid substance containing the α-amylase inhibiting substances prepared by the processes of the invention can be used intact as a dieting agent, or may be further formulated into liquid preparations and solid preparations such as granules and tablets together with conventional adjuvants. The adjuvants include known excipients, fillers, lubricants, binders, perfumes, coloring agents and other additives.

For the purpose of using as a dieting agent, the preparations containing α-amylase inhibiting substances can be administered in the form of liquid, tablet or granule usually in an amount equivalent to 1,000 U or above, preferably 3,000–30,000 U of the saliva α-amylase inhibiting substance per day in adults.

A preferred preparation means is a wet kneading method which comprises adding to an α-amylase inhibiting substance-containing solid substance, 15 to 80% by weight, preferably 30 to 50% by weight of ethanol or 15 to 60% by weight, preferably 25 to 45% by weight of a mixed solution of water and ethanol and granulating a resulting mixture for the preparation of tablets or granules. To improve the disintegration of tablets, a disintegrating agent is preferably added in an amount of at least 10% by weight, preferably at least 25% by weight. The disintegrating agents include carboxymethyl cellulose, calcium carboxymethyl cellulose, starch, hydroxypropyl starch, lactose or calcium hydrogen phosphate or a mixture thereof.

The invention is further illustrated by the following non-limitative examples.

EXAMPLE 1

As the starting material was used a waste liquid of wheat flour from removal of gluten and starch. Inhibiting activity of the waste liquid was 8.41 for human saliva amylase (U/mg protein) and 3.55 for human pancreatic juice protein (U/mg protein). Into 800 lit. of the waste liquid were introduced steam over a period of 15 min. and the liquid was heated to 90° C. Subsequently, 900 lit. of the resulting solution were centrifuged continuously (3000 G) to remove modified proteins. The resulting clear supernatant was filtered with filters having a pore size of 3 μm and 1 μm, respectively, to yield 850 lit. of a clear solution. The solution was then passed through a microfiltration membrane having a pore size of 0.2 μm for sterilization. The solution was then concentrated through Romicon PM-100 ultrafiltration membrane (membrane area of 2.5 m$^2$, two membranes) to about 1/10 of its original volume. A concentration temperature was 70° C., and an inlet pressure of the membrane was about 2 kg/m$^2$. The solution was circulated for about 3 hours.

Subsequently, the concentrated solution was spray-dried to yield 4.1 g of powders. Inhibiting activity of the product was 11.8 for human saliva amylase (U/mg protein) and 5.02 for human pancreatic juice amylase.

EXAMPLE 2

300 g of the powders obtained in Example 1 and 120 g of ethanol were kneaded in a kneader ("PNV-5" manufactured by Irie Trading Co., Ltd.) for 20 min. The kneaded mass was granulated (0.8 mm) using a biaxial granulator ("EXD-60" manufactured by Fuji Powdal Co., Ltd.), dried on shelf at 60° C. for 4 hours and then grated (14 mesh) in a crush granulator ("Power Mill P-02S" manufactured by Sanei Manufacturing Co., Ltd.) to form granules.

EXAMPLE 3

300 g of the powders obtained in Example 1 and 90 g of a mixed solution of water and ethanol (weight ratio of 4:6) were kneaded in a kneader ("PNV-5" manufactured by Irie Trading Co., Ltd.) for 20 min. The kneaded mass was granulated (2 mm herringbones) using a crush granulator ("Power Mill P-02S" manufactured by Sanei Manufacturing Co., Ltd.), dried on shelf at 60° C. for 4 hours and grated (20 mesh) in a crush granulator ("Power Mill P-02S" manufactured by Sanei Manufacturing Co., Ltd.). To the granules were added 9.0 g of sucrose fatty acid esters ("Ryoto Sugar Ester S-370" manufactured by Mitsubishi Kasei Corporation), and the mixture was tabletted using a tablet machine ("Clean Press Collect 19" manufactured by Kikusui Manufacturing Co., Ltd.) to form tablets, each weighing 309 mg.

EXAMPLE 4

To the granules obtained in Preparation Example 1 was added hydroxypropyl starch or calcium carboxymethyl cellulose. The mixture was tabletted to form tablets.

A disintegration of the tablets was evaluated according to the disintegration test method described in the Pharmacopoeia of Japan (Revised Edition XI). The results are shown in Table 1.

TABLE 1

| Concentration of the disintegrating agent and disintegration time (minute) | | | | |
|---|---|---|---|---|
| | 0% | 10% | 30% | 50% |
| Hydroxypropyl starch | 90 | 70 | 53 | 44 |
| Calcium carboxymethyl cellulose | 90 | 54 | 25 | 7 |

EXAMPLE 5

Influence upon blood glucose level was investigated using mice (6 weeks age, ddY species, male, 20-30 g) (test groups of each 6 animals).

The mice (normal blood glucose level, about 200 mg glucose/100 ml) was put in test after fasted for 17 hours. The blood glucose level after the fasting was 70-80 mg glucose/100 ml.

An aqueous solution of soluble starch (Wako Junyaku, first Grade) was administered orally, forcibly through a stomach probe. The soluble starch and a powdery product obtained in Example 1 were thoroughly mixed in a mortar, and admixed portionwise with distilled water to prepare an aqueous solution for administration. At minutes 0, 15, 30, 45, 60, 120, 180 and 240 after the administration, 50 μl each of blood was drawn from the eyeground capillary vein by Hematocrit Capillary Tube (manufactured by Terumo). The capillary tube was sealed at one end, and the tube was centrifuged at 12000 rpm for 5 min. using a high speed centrifuge for the measurement of hematocrit ("KH-30A" manufactured by Kubota Co., Ltd.) to separate serum. For the measurement of blood glucose level in serum was used RaBA Mark II, Unikit Glucose E (manufactured by Chugai Pharmaceutical Co., Ltd.). 20 μl of the serum was added to a color-developing solution, the mixture was pre-warmed at 37° C. for 5 min. and 50 μl of an enzyme solution was added thereto. The mixture was warmed at 37° C. for 20 min. for color development. After the color development, blood glucose level was measured using RaBA Mark II.

As it was expected that increase in blood glucose level would be induced by such operations as oral administration through a probe and drawing of blood from the eyeground vein, distilled water was orally administered as a control, and blood was drawn at minutes 0, 15, 30, 45, 60, 120, 180 and 240 after the oral administration for examination of the variation in blood glucose level. It was found that an increase in blood glucose level to about 50 mg glucose/100 ml was induced as a result of operations of oral administration and blood drawing only (refer to FIG. 1). Next, increase in blood glucose level caused by soluble starch was examined to find that oral administration of soluble starch (2.5 g/kg) caused an increase in blood glucose level of about 200 mg glucose/100 ml as compared with the administration of distilled water. The increase in blood glucose level reached a peak (about 380 mg glucose/100 ml) 30 minutes after the administration and was depressed with elapse of time (FIG. 1). On the other hand, when soluble starch (2.5 g/kg) and the powdery product obtained in Example 1 (10 mg/mouse) were orally administered at the same time, increased blood glucose level reached a peak level (300 mg glucose/100 ml) 15 minutes after the administration, the peak level being lower by about 80 mg glucose/100 ml than that for the administration of soluble starch alone.

Acute Toxicity Test

To groups of each 5 ddY male and female mice (5 weeks age), were orally administered the aqueous extract of wheat flour (experimental section), raw wheat flour (control section) and distilled water (blank section) and the mice were observed for 14 days. The animals received the agent in 10% (w/v) aqueous solution at a dose of 50 ml/kg. No toxic symptoms was observed in any section. No significant difference in body weight change was measured for the three sections. Neither gross pathological change nor accumulation of the agent in viscera was also observed.

What is claimed is:

1. A process of preparing an alpha-amylase inhibiting substance from wheat which comprises heat treating a supernatent fraction of an aqueous extract of wheat or wheat flour at a temperature of 70°-95° C. for a time sufficient to modify unnecessary protein contaminants in the supernatent fraction, removing the modified protein from said fraction, and subjecting the resulting aqueous solution containing an alpha-amylase inhibiting substance to a concentration treatment using an ultrafiltration membrane.

2. A process of claim 1 wherein the aqueous solution containing an α-amylase inhibiting substance is subjected to a filtration and sterilization treatment prior to the concentration treatment using an ultrafiltration membrane.

3. A process of claim 1 or 2 which further comprises drying of the concentrated solution containing an α-amylase inhibiting substance.

4. A process of claim 1 wherein the ultrafiltration membrane include the membrane of polyacrylonitrile, polyolefin, polysulfone, polyimide or polypropylene materials, each having a fractionation molecular weight of 5,000, 6,000, 8,000, 10,000, 13,000, 20,000, 30,000, 50,000, 100,000 and 200, 000 Dalton cut off.

5. A process of claim 1 wherein the ultrafiltration membrane is a polysulfone ultrafiltration membrane having a fractionation molecular weight of 100,000 Dalton cut off.

* * * * *